United States Patent [19]

Ueno et al.

[11] Patent Number: 5,001,154

[45] Date of Patent: Mar. 19, 1991

[54] FERVESCENCE COMPOSITION

[75] Inventors: Ryuzo Ueno; Ryuji Ueno, both of Nishinomiya; Tomio Oda, Sanda, all of Japan

[73] Assignee: K.K. Ueno Seiyaku Oyo Kenkyujo, Osaka, Japan

[21] Appl. No.: 440,449

[22] Filed: Nov. 22, 1989

Related U.S. Application Data

[63] Continuation-in-part of Ser. No. 193,627, May 13, 1988, abandoned.

[30] Foreign Application Priority Data

May 15, 1987 [JP] Japan ................ 62-119367
Sep. 17, 1987 [JP] Japan ................ 62-235962

[51] Int. Cl.$^5$ ................ A61K 31/215; A61K 31/557
[52] U.S. Cl. ................ 514/530; 514/523
[58] Field of Search ................ 514/530, 573

[56] References Cited

U.S. PATENT DOCUMENTS 4,080,458 3/1978 Radunz et al. ................ 514/573 X
4,621,100 11/1986 Lund et al. .

FOREIGN PATENT DOCUMENTS 0153858 9/1985 European Pat. Off. .

OTHER PUBLICATIONS

Chemical Abstracts 79:74055Z 1923.
Arch. Int. Pharmacodyn. 197, 31-36 (1972).
Proceedings of the Physiological Society, Jan. 1970, pp. 76P-77P.
Dialog Information Services, File 155, Medline 66-88, Accession No. 03856313; M. J. DASCOMDE et al.
Chemical Abstracts, vol. 79, No. 1, 9th Jul. 1973, p. 112, No. 1137t.
Prostaglandins, vol. 9, No. 3, Mar. 1975, pp. 361-368; W. G. Clark et al., p. 365.

Primary Examiner—Leonard Schenkman
Attorney, Agent, or Firm—Sughrue, Mion, Zinn, Macpeak & Seas

[57] ABSTRACT

This invention provides a fervescence composition containing 15-keto-PHEs separated from any substantial activity such as decrease of blood pressure.

42 Claims, 12 Drawing Sheets

FERVESCENCE COMPOSITION

This is a continuation-in-part of application Ser. No. 07/193,627, filed May 13, 1988 abandoned.

BACKGROUND OF THE INVENTION

This invention relates to a fervescence composition containing 15-keto-prostaglandin E and their derivatives.

Development of a drug for recovering from hypothermia occurred after hypothermic operation such as operation of cardiovasculum and brain surgery, hypothermia caused by a decline of basal metabolism such as thyroid hormone hyposecretion, hypothermia by disorder of the brain or hypothermia caused by serious bleeding and disorder of consciousness occurred by, for example, a traffic accident as well as development of a drug for preventing from hypothermia have been desired.

On the other hand, prostaglandins are known to have various pharmacological activities, antiplatelet aggregation activity, myometruim stimulating activity, antiulcer activity and the like. Among prostagrandins, for example, prostaglandin $E_2$ is known to have fervescence activity. However, it cannot be used as a drug for recovering body temperature since it strongly decreases the blood pressure at the same time. On the other hand, 15-keto-prostaglandin E (noted as 15-keto-PGE hereafter) and 13,14-dihydro-15-keto-prostaglandin E (noted as 13,14-dihydro-15-keto-PGE hereinafter) are known as a substance naturally produced by an enzyme in the metabolism of prostaglandin E (noted as PGE hereinafter) in a living body. These 15-keto-PGE have been considered to be physiologically and pharmacologically inactive substances (Acta Physiologica Scandinavica, Vol. 66, pp 509 (1966)). It has never been recognized that these 15-keto-PGE have fervescence activity.

SUMMARY OF THE INVENTION

Figure 1:
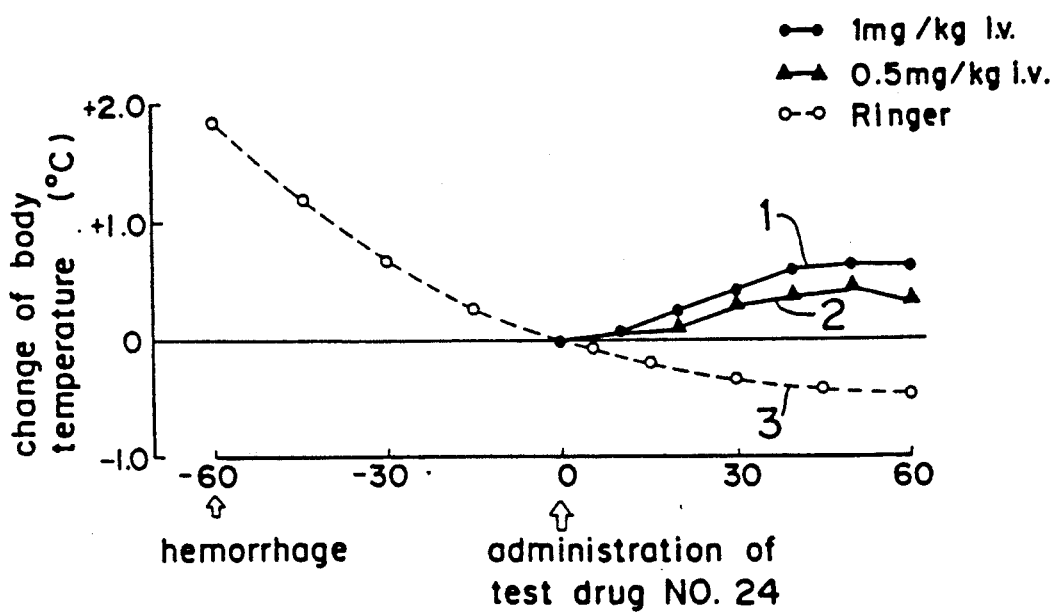
FIG. 1 shows change of body temperature before and after administration of a test drug 24, (13,14-dihydro-15-keto-$PGE_2$ ethyl ester) to a rat loaded with bloodletting.

This invention provides a fervescence composition containing 15-keto-prostaglandin E and their derivatives (noted as 15-keto-PGEs as including the derivatives hereinafter), which are separated from any substantial activity such as decrease of blood pressure. Ester type of 15-keto-PGEs on the end carboxyl group of α-chain shows fervescence activity even by peripheral administration.

DETAILED DESCRIPTION OF THE INVENTION

This invention provides a fervescence composition which comprises 15-keto-PGEs as an active ingredient.

In this invention, 15-keto-PGEs include 15-keto-PGEs of which the carbon atom of 15-position is carbonyl, and 13,14-dihydro-15-keto-PGEs of which the bond between carbon atoms of 13- and 14-position is saturated and the carbon atom of 15-position is carbonyl. Therefore, this invention includes every prostaglandin E as long as it is in 15-keto or 13,14-dihydro-15-keto form in the prostaglandin skeleton structure and is not limited by other additional skeleton structure or substituents.

In the present specification 15-keto-PGEs are expressed according to the following nomenclature. The 15-keto-PGEs have a following basic structure:

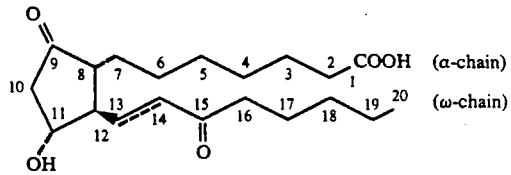

and the position number of carbon atom constituting α-chain, ω-chain and five members ring in the prostaglandin skeleton structure is used as it is in the nomenclature. That is, the position number of the carbon atom in the skeleton structure is started from the carbon atom constituting carboxylic acid of the terminal position of α-chain through the five members ring to ω-chain i.e. 1 to 7 are attached to the carbon atoms in the α-chain in this order, 8–12 are attached to the carbon atoms in the five members ring, and 13–20 are attached to the carbon atoms in the ω-chain. In the compound whose carbon number in α-chain is less than 7 the position number is simply eliminated from 2 to 7 in this order without any change of the position number of the other carbons. In other word 15-keto-PGEs having 6 carbon atoms in the α-chain have no position of 2, i.e. 15-keto-PGEs of such compound are not renamed as 14-keto-PGEs. In case that carbon atoms increase in the α-chain the carbon chain increased is nominated as a substituent on the carbon of position number 2 without any change of the position number of the other carbons. Therefore, 15-keto-PGEs having 8 carbon atoms in the α-chain are nominated as 15-keto-2-decarboxy-2-acetic acid-PGEs. In case that the number of the carbon in the ω-chain decreases the position number is nominated as reducing it from the carbon of position number 20 one by one. In case the number of the carbon atoms in the ω-chain increases, the increased carbon chain is nominated as a substituent on the carbon of position number 20. That is, 15-keto-PGEs having 10 carbon atoms in the ω-chain is nominated as 15-keto-20-ethyl-PGEs.

The above formula expresses a specific configuration which is most typical one, and in this specification compounds having such a configuration are expressed without any descriptions about it.

PGE have a hydroxy group on the carbon atom of 11-position in general, but in the present specification term "PGEs" includes prostaglandins having other group instead of said hydroxyl group of normal PGE. Such PGEs are called as 11-dehydroxy-11-substituent-PGEs, for instance, 11-dehydroxy-11-methyl-PGEs in case of the substituent being a methyl group.

PGEs are classified to $PGE_1$ and $PGE_2$ according to the bonds between carbon atoms of 5, 6 and 7 position.

$PGE_1$ and its derivatives (referred to as $PGE_1$s hereinafter) are nominated to a group of compounds in which the bond between carbon atoms of 5 and 6 position, and of 6 and 7 position are a single bond respectively. $PGE_2$ and its derivatives (referred to as $PGE_2$s hereinafter) are called to a group of compounds in which the bond between carbon atoms of 5 and 6 position is a trans-double bond. Therefore, PGEs having a structure of

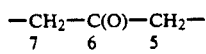

is nominated as 6-keto-PGE$_1$s, and PG having a structure of

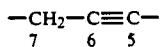

is called as 5,6-dehydro-PGE$_2$s.

The fervescence activity is remarkably expressed in 15-keto-PGEs represented by the following formula:

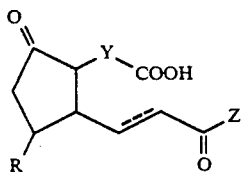

wherein R is a hydroxyl group, a hydroxyalkyl group, or an alkyl group; Y is a saturated or unsaturated hydrocarbon moiety having 2–6 carbon atoms wherein a portion of carbon atoms constituting the hydrocarbon moiety may be carbonyl or a portion of hydrogen atoms constituting the hydrocarbon moiety may be substituted with other atoms or groups; Z is a saturated or unsaturated hydrocarbon moiety which may constitute a straight chain or a ring, wherein a portion of hydrogen atoms of the hydrocarbon moiety may be substituted with other atoms or groups; or physiologically acceptable salts thereof or esters which are esterified on the terminal carboxyl group.

Y represents a saturated or an unsaturated hydrocarbon moiety having 2–6 carbon atoms, include an aliphatic hydrocarbon such as an alkyl group, an alkenyl group, an alkynyl group and the like. Y may preferably be hydrocarbon chain having 6 carbon atoms.

Examples of PGEs of which Y is an unsaturated hydrocarbon moiety are PGE$_2$s, 5,6-dehydro-PGE$_2$s, PGEs of which the bond between 2- and 3-position is unsaturated, and the like.

A portion of carbon atoms constituting hydrocarbon moiety represented by Y may be carbonyl, whose typical examples are 6-keto-PGE$_1$s in which the carbon atom of 6-position is carbonyl.

The hydrocarbon moiety represented by Y may be substituted with other atoms or groups, for example, halogen atoms such as a fluorine atom, a chlorine atom, typically a fluorine atom; an alkyl group such as methyl, ethyl; a hydroxyl group and the like. Typical examples of such substituents are 15-keto-PGEs having an alkyl group on the carbon atom of 3-position.

Z represents a saturated or an unsaturated hydrocarbon moiety having 1–10 carbon atoms. The hydrocarbon moiety may be an aliphatic hydrocarbon or a cyclic hydrocarbon itself or in part. The hydrocarbon moiety represented by Z may be substituted with other atoms or groups.

The number of the carbon atoms of Z is preferably 3–7 in straight chain. PGEs of which carbon numbers of Z are 5 correspond to typical PGs. Therefore, the PGEs of which carbon numbers of the hydrocarbon moiety represented by Z are 6 or more than 6 are nominated as PGEs having a substituent on the carbon atom of 20-position. That is, PGEs of which the number of carbon atoms of Z is 6 are nominated as 20-methyl-PGEs.

Though the hydrocarbon moiety represented by Z may have substituents at any position, a saturated hydrocarbon is more preferable. Examples of the hydrocarbon moiety having a cyclic ring are a cyclopentyl or a cyclohexyl containing the carbon atom of 16- or 17-position itself as a ring constituting member.

The hydrocarbon moiety represented by Z may be substituted with other atoms or groups, for example, halogen atoms such as a fluorine atom or a chlorine atom; an alkyl group such as methyl, ethyl, isopropyl, isopropenyl; an alkoxy group such as methoxy, ethoxy; a hydroxyl group; a phenyl group; a phenoxy group and the like. The position of the substituent may be preferably the carbon atom of 16-, 17-, 19- and/or 20-position, but it is not restricted. Examples of preferable compounds include one which has one or two, different or identical atom(s) and/or groups, for example, halogen atoms such as a fluorine atom; an alkyl group such as methyl, ethyl; an aromatic group which may have substituent such as phenyl, benzyl, phenoxy; a hydroxyl group on the carbon atom of 16-position. Other examples of preferable compounds include one which has a cycloalkyl group such as cyclopentyl, cyclohexyl which contains the carbon atom of 16-position as a constituent of the cyclic ring; an alkyl group such as methyl, ethyl on carbon atom of 17- or 19-position; an alkyl group such as methyl, ethyl, isopropyl, isopropenyl; an alkoxy group such as methoxy, ethoxy, propoxy on the carbon atom of 20-position.

A generic name of PGEs is used to compounds having a prostanoic acid structure in which the carbon atom of 11-position has a hydroxyl group, and the carbon atom of 9-position is carbonyl. In the present specification a prostanoic acid compound in which the hydroxyl group on the carbon atom of 11-position is substituted with a hydroxyalkyl group or an alkyl group is also called as PGEs. Therefore, the 15-keto-PGEs of the present invention include compounds in which R of the general formula (I) represents a hydroxyalkyl group or an alkyl group, for example, a hydroxy group such as hydroxymethyl, 1-hydroxyethyl, 2-hydroxyethyl, 1-methyl-1-hydroxyethyl; an alkyl group such as methyl, ethyl.

The steric configuration of R with respect to the carbon of 11-position may be α or β or mixture thereof.

The 15-keto-PGEs of the present invention may be a physiologically acceptable salt or ester which is esterified on the terminal carboxyl group.

The cation to be used for producing such salts may be an alkaline metal such as sodium and potassium; an alkaline earth metal such as calcium or magnesium; amines such as methylamine, dimethylamine, cyclopentylamine, benzylamine, piperidine, monoethanolamine, diethanolamine, monomethylmonoethanolamine, tromethamine, lysine, ammonium, tetraalkylammonium salts and the like.

Useful ester of 15-keto-PGEs may include a saturated or an unsaturated lower alkyl ester which may have a branched chain such as methyl, ethyl, propyl, n-butyl, isopropyl, t-butyl, 2-ethylhexyl, allyl and the like; an aliphatic cyclic ester such as cyclopropyl, cyclopentyl, cyclohexyl and the like; an aromatic ester which may have substituents such as benzyl, phenyl and the like; a hydroxyalkyl or an alkoxyalkyl ester such as hydroxyethyl, hydroxyisopropyl, methoxyethyl, ethoxyethyl, methoxyisopropyl and the like; a trialkylsilyl ester such as trimethylsilyl, triethylsilyl and the like; a heterocyclic ester such as tetrahydropyranyl and the like. Preferable esters for the present invention are a lower alkyl ester which may have a branched chain, for instance, methyl, ethyl, propyl, n-butyl, isopropyl, t-butyl; a benzyl ester; a hydroxyalkyl ester such as hydroxyethyl, hydroxy isopropyl; and the like.

15-keto-PGEs of the present invention may includes various kinds of isomers such as tautomeric isomers, optical isomers, geometric isomers and the like. As an example of such isomers there is exemplified a tautomeric isomer between the hydroxyl group at carbon atom of 11-position and the carbonyl group on carbon atom of 15-position of 15-keto-PGEs. The latter tautomeric isomer is liable to be caused in 15-keto-PGEs having an electron attractive group such as fluorine atom at 16-position.

A hemiacetal, a tautomeric isomer between the hydroxyl group at carbon atom of 11-position and the carbonyl group on carbon atom of 15-position, may be sometimes formed in a subclass of the 15-keto PGEs, which subclass consists of 13,14-dihydro-15-keto-PGEs of this invention, and an equilibrium mixture of the compound of R being a hydroxyl group and a hemiacetal may be given. Such an equilibrium mixture or the tautomeric isomer is also included in the subclass of 13,14-dihydro-15-keto-PGEs of the present invention.

Most preferable group of 15-keto-PGEs of the present invention is 15-keto-PGEs having a double bond between carbon atoms of 5- and 6-position or forming carbonyl group at 6-position. Another preferable group of 15-keto-PGEs of the present invention is one having 8-10 carbon atoms in the ω-chain. Another preferable group of 15-keto-PGEs of the present invention is one which has (a) halogen atom(s) or (an) alkyl substituents at 16-position. Another preferable one includes 15-keto-PGEs which have a lower alkyl, especially methyl substituent at 19-position of ω-chain having carbon atoms of more than 7 in the skeleton chain.

Concrete examples of most preferable 15-keto-PGEs are 13,14-dihydro-15-keto-19-methyl-$PGE_2$ alkyl ester, 13,14-dihydro-15-keto-16R,S-fluoro-$PGE_2$ alkyl ester, 13,14-dihydro-15-keto-16R,S-fluoro-11-dehydroxy-11R-methyl-$PGE_2$ alkyl ester, 13,14-dihydro-15-keto-20-methyl-$PGE_2$ alkyl ester, 13,14-dihydro-15-keto-16R,S-methyl-$PGE_2$ alkyl ester, 13,14-dihydro-6,15-diketo-19-methyl-$PGE_1$ alkyl ester, 13,14-dihydro-6,15-diketo-16R,S-fluoro-$PGE_1$ alkyl ester, 13,14-dihydro-6,15-diketo-16R,S-fluoro-11-dehydroxy-11R-methyl-$PGE_1$ alkyl ester, 13,14-dihydro-6,15-diketo-20-methyl-$PGE_1$ alkyl ester and 13,14-dihydro-6,15-diketo-16R,S-methyl-$PGE_1$ alkyl ester.

In the present specification PGEs are named based on a prostanoic acid skeleton, but it can be named according to IUPAC nomenclature, according to which, for instance, PGE, is nominated as 7-{(1R,2R,3R)-3-hydroxy-2-[(E)-(3S)-3-hydroxy-1-actenyl]-5-oxo-cyclopentyl}-heptanoic acid; $PGE_2$ is nominated as (Z)-7-((1R,2R,3R,)-3-hydroxy-2-[(E)-(3S)-3-hydroxy-1-octenyl]-5-oxo-cyclopentyl)-hept-5-enoic acid; 13,14-dihydro-15-keto-16R,S-fluoro-$PGE_2$ is nominated as (Z)-7-{(1R,2R,3R)-3-hydroxy-2-[(4R,4S)-4-fluoro-3-oxo-1-octyl]-5-oxo-cyclopentyl}-hept-5-enoic acid; 13,14-dihydro-15-keto-20-ethyl-11-dehydroxy-11R-methyl $PGE_2$ methyl ester is nominated as Methl 7-{(1R,2S,3R)-3-methyl-2-[3-oxo-1-decyl]-5-oxo-cyclopentyl}-kept-5-enoate; and 13,14-dihydro-6,15-diketo-19-methyl-$PGE_2$ ethyl ester is nominated as Ethyl 7-{(1R,2R,3R)-3-hydroxy-2-(7-methyl-3-oxo-1-octyl)-5-oxo-cyclopentyl)-6-oxo-heptanoate.

The 15-keto-PGEs show fevescence activity by intracerebroventricular administration whether carboxylic acid type compounds or carboxy ester type compounds. However, the carboxylic acid type compounds show no fervescence activity by peripheral administration such as intravenous injection or oral administration. On the other hand, carboxy ester type compounds shows fervescence activity even when administered peripherally such as intravenously and orally. The ester compound of which R is a lower alkyl group such as methyl or ethyl group shows strongest fervescence activity.

Improvement of body mechanism such as temperature rising is brought on to the animal being out of normal condition such as normal temperature, for example, in the shock state by such as bleeding. Namely, the compound is effective to the animal out of homeostasis or under anesthesia.

The 15-keto-PGEs used in this invention may be prepared, for example, by the method noted in Japanese Patent Application No. 18326/1988. The disclosure on it is constructed to be a part of this specification.

A practical preparation of the 13,14-dihydro-15-keto PGEs involves the following steps; as shown in the synthetic chart (I), reaction of the aldehyde (2) prepared by the Colins oxidation of commercially available Corey lactone (1) with dimethyl (2-oxoheptyl)phosphate anion to give α,β-unsaturated ketone (3), reaction of the α,β-unsaturated ketone (3) to the corresponding saturated ketone (4), protection of the carbonyl group of the ketone (4) with a diol to the corresponding ketal (5), and deprotection of the p-phenylbenzoyl group to give the corresponding alcohol (6) followed by protection of the newly generated hydroxy group with dihydropyrane to give the corresponding tetrapyranyl ether (7). According to the above process, a precursor of PGEs of which ω chain is a 13,14-dihydro-15-keto-alkyl group is prepared. Where a 13,14- unsaturated PGE is desired, the step of reacting the alpha, beta-unsaturated ketone (3) to the corresponding saturated ketone (4) can be omitted. Naturally, in that instance, the carbonyl group of the ketone (3) would be protected with a diol, etc.

Using the above tetrapyranyl ether (7), 6-keto-$PGE_1$s (15) of which a group constituted with carbon atoms of 5-, 6- and 7-position is

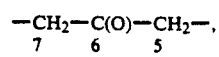

may be prepared in the following steps; reduction of the tetrapyranyl ether (7) with, for example, diisobutyl aluminum hydride to give the corresponding lactol (8), reaction of the lactol (8), with the ylide generated from (4-carboxybutyl)triphenyl phosphonium bromide followed by esterification, cyclization between the double bond between at carbon atoms of 5- and 6-position and the hydroxyl group on carbon atom of 9-position with NBS or iodine to give the halogenated compound (11), dehalogenation of the compound (11) with, for example, DBU to give the 6-keto compound (13) followed by Jhones oxidation and removal of the protecting groups.

Furthermore, PGE$_2$s (19) of which a group constituted with carbon atoms of 5-,6- and 7-position is

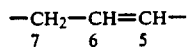

may be prepared in the following steps; as shown in the synthetic chart II, reduction of the above the tetrapyranyl ether (7) to give the lactol (8), reaction of the resultant lactol (8) with the ylide generated from (4-carboxybutyl)triphenyl phosphonium bromide to give the carboxylic acid (16) followed by esterification of (17), Jhones oxidation of the esters (17) to give the compound (18), and removal of the protecting groups.

Using the above the tetrapyranyl ether (7) as starting material, the compound having the group of

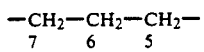

may be prepared by using the same process for preparing PGE$_2$s having the group of

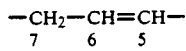

and applying the resultant compound (18) to catalytic reduction for reducing the double bond between at the 5- and 6-position followed by removal of the protection groups.

Synthesis of 5,6-dehydro-PGE$_2$s having a group of

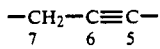

may be carried out by alkylation of the resulting a copper enolate generated after 1,4-addition of a monoalkylcopper complex or a dialkylcopper complex of the following formula:

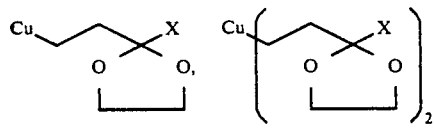

to 4R-t-butyldlmethylsilyloxy-2-cyclopenten-1-one with 6-alkoxycarbonyl-1-iodo-2-hexyne or the derivatives.

The 11-β type PGEs can be prepared according to the synthetic chart III. The 15-keto-PGEs of this invention may be used as a medicine for animals and human beings and usually applied systemically or locally by the method of oral administration, oral administration by spraying, intravenous injection (including instillation), subcutaneous injection, suppository and the like. Dose is determined depending on the animal to be treated, the human patient, age, body weight, symptom, therapeutic effect, administration route, treating time and the like, but is preferably 0.001-500 mg/Kg.

As solid composition of this invention for oral administration, tablets, powders, granules and the like are included. The solid composition containing one or more active substances is mixed with at least an inactive diluent such as lactose, mannitol, glucose, hydroxypropyl cellulose, fine crystalline cellulose, starch, polyvinyl pyrolidone, magnesium aluminate metasilicate. The composition may contain except for the inactive diluent other additives such as lubricants (e.g. magnesium stearate), a disintegrator (e.g. cellulose calcium gluconate), a stabilizer (e.g. α-, β- or γ-cyclodextrin, etherated dextrin (e.g. dimethyl-α-, dimethyl-β-, trimethyl-β- or hydroxypropyl-β-cyclodextrin), branched cyclodextrin (e.g. glucosyl- or maltosylcyclodextrin), formyl cyclodextrin, sulfur-containing cyclodextrin or misoprotol). Such cyclodextrins may form an inclusion compound with 15-keto-PGEs in some cases to increase the stability of the compounds. The stability may be often increased by forming lyposome with phospholipid. Tablets and pills may be coated with an enteric or gastroenteric film such as white sugar, gelatin, hydroxypropylcellulose, hydroxypropylmethylcellulose phthalate and the like, if necessary, and furthermore they may be covered with two or more layers. Additionally, the composition may be in the form of capsules made of substance easily absorbed such as gelatin.

Liquid compositions for oral administration include pharmaceutically acceptable emulsions, solutions, suspensions, syrups, elixirs and the like and contain a generally used inactive diluent such as purified water or ethyl alcohol. The composition may contain additives such as wetting agents and suspending agents as well as sweeteners, flavors, aromatics and preservatives.

The compositions for oral administration may contain one or more active substance.

The injection of this invention for non-oral administration includes sterile aqueous or nonaqueous solutions, suspensions, and emulsions. Diluents for the aqueous solution or suspension contain, for example, distilled water for injection, physiological saline and Ringer's solution. Diluents for the nonaqueous solution and suspension contain, for example, propylene glycol, polyethylene glycol, vegetable oils such as olive oil, alcohols such as ethanol and polysorbates. The composition may contain other additives such as preservatives, wetting agents, emulsifying agents, dispersing agents and the like. These are sterilized by filtration through, e.g. a bacteria-preventing filter, compounding with a sterilizer, gas sterilization or radiation sterilization. These can be prepared by producing a sterile solid composition and dissolving it into sterilized water or a sterilized solvent for injection before use.

EXAMPLE 1 fervescence activity by intracerebroventricular injection

Wister male rats (8 weeks old) were used as test animals.

Rats were applied to anesthesia by intraperitoneal injection with 1.25 g/kg of urethane and a stainless guide cannula was inserted into the lateral ventricle for administration of a test drug according to Pellegrino's Rat brain atras.

Each test drug was dissolved into an artificial cerebrospinal fluid and 400 ng as drug in 3 µl was injected through the injection cannula for 15 seconds. The artificial cerebrospinal fluid alone was injected as control. Body temperature was measured continuously at the rectum. Rising of body temperature is shown by the rising degree (°C.) from the temperature before administration. The results are shown in Table 1.

TABLE 1

| Test Drug | Rising of body temperature |
|---|---|
| 22 | +0.7 |
| 23 | +0.4 |
| 24 | +0.5 |
| 26 | +0.1 |
| 1 | +0.4 |
| 2 | +0.4 |
| 6 | +0.8 |
| 7 | +0.6 |
| 8 | +0.4 |
| Control | 0 |

EXAMPLE 2 fervescence activity by intravenous injection

Test animals were Wister male rats (8 weeks old) weighing 200±10 g. The rats were applied to anesthesia by intraperitoneal injection of 1.25 g/kg of urethane. Each test drug was dissolved into ethyl alcohol. The ethyl alcohol solution was diluted with Ringer's solution at least 50 times just before use and 1 mg/kg of the each test drug was intravenously administered. Body temperature was measured in the same manner as in Example 1.

Ringer's solution containing ethyl alcohol was administered as control. Rising of body temperature is shown by the rising degree (°C.) from the temperature before administration. The results are shown in table 2.

TABLE 2

| Test Drug | Rising of Body Temperature (°C.) |
|---|---|
| 1 | 0 |
| 2 | +0.9 |
| 3 | 0 |
| 4 | +0.8 |
| 5 | +0.4 |
| 6 | 0 |
| 7 | +0.8 |
| 8 | +0.6 |
| 9 | +0.7 |
| 10 | +0.2 |
| 11 | +1.5 |
| 12 | +0.9 |
| 13 | +1.1 |
| 14 | +1.0 |
| 15 | +0.7 |
| 16 | +0.8 |
| 17 | +0.4 |
| 18 | +0.7 |
| 19 | +1.0 |
| 20 | +1.3 |
| 21 | +1.1 |
| 22 | 0 |
| 23 | +1.0 |
| 24 | +0.5 |
| 25 | +0.2 |
| 26 | +0.2 |
| 27 | +0.3 |
| 28 | +0.4 |
| 29 | +1.0 |
| 30 | +1.7 |
| 31 | +1.0 |
| 32 | +1.4 |
| 33 | +0.9 |
| 34 | +1.0 |
| 35 | +1.0 |
| 36 | +0.6 |
| 37 | +0.2 |
| 38 | +0.3 |
| 39 | +0.9 |
| 40 | +1.4 |
| 41 | +0.8 |
| 42 | +1.4 |
| 43 | +0.2 |
| 44 | +0.2 |
| 45 | +2.0 |
| 46 | +0.6 |
| 47 | +0.3 |
| 48 | +0.2 |
| 49 | +0.2 |
| 50 | +0.2 |
| 51 | +0.2 |
| 52 | +0.2 |
| 53 | +0.5 |
| 54 | +0.2 |
| 55 | +0.2 |
| 56 | +1.0 |
| 57 | 0 |
| 58 | +0.7 |
| 59 | +1.2 |
| control | 0 |

Test drug (Figure number n.m.r. charts of corresponding compounds are shown in brackets after the compound names respectively.)

Figure 3:
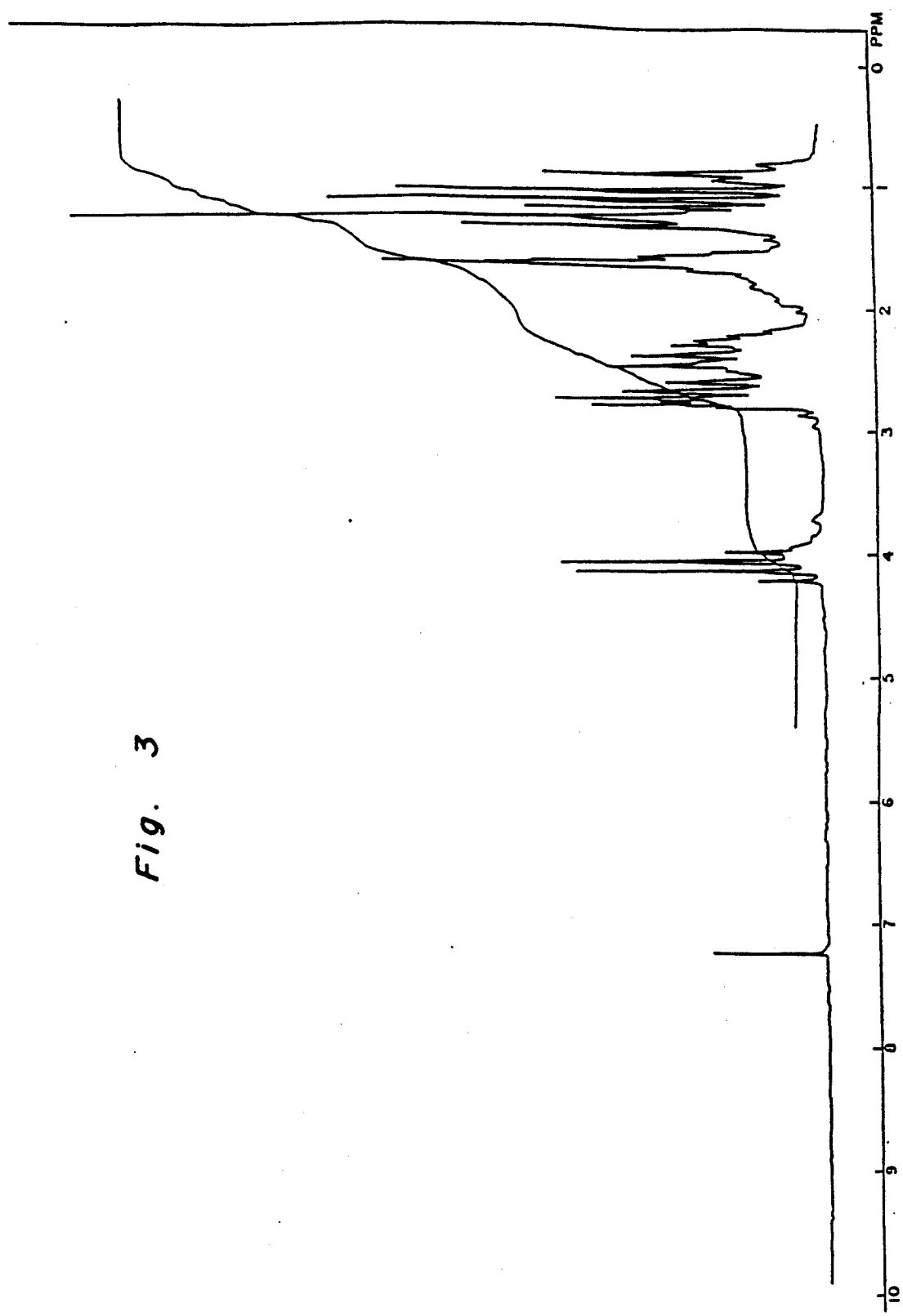
FIGS. 3–13 are n.m.r. charts of 13,14-dihydro-15-keto-PGEs of the present invention.
Figure 4:
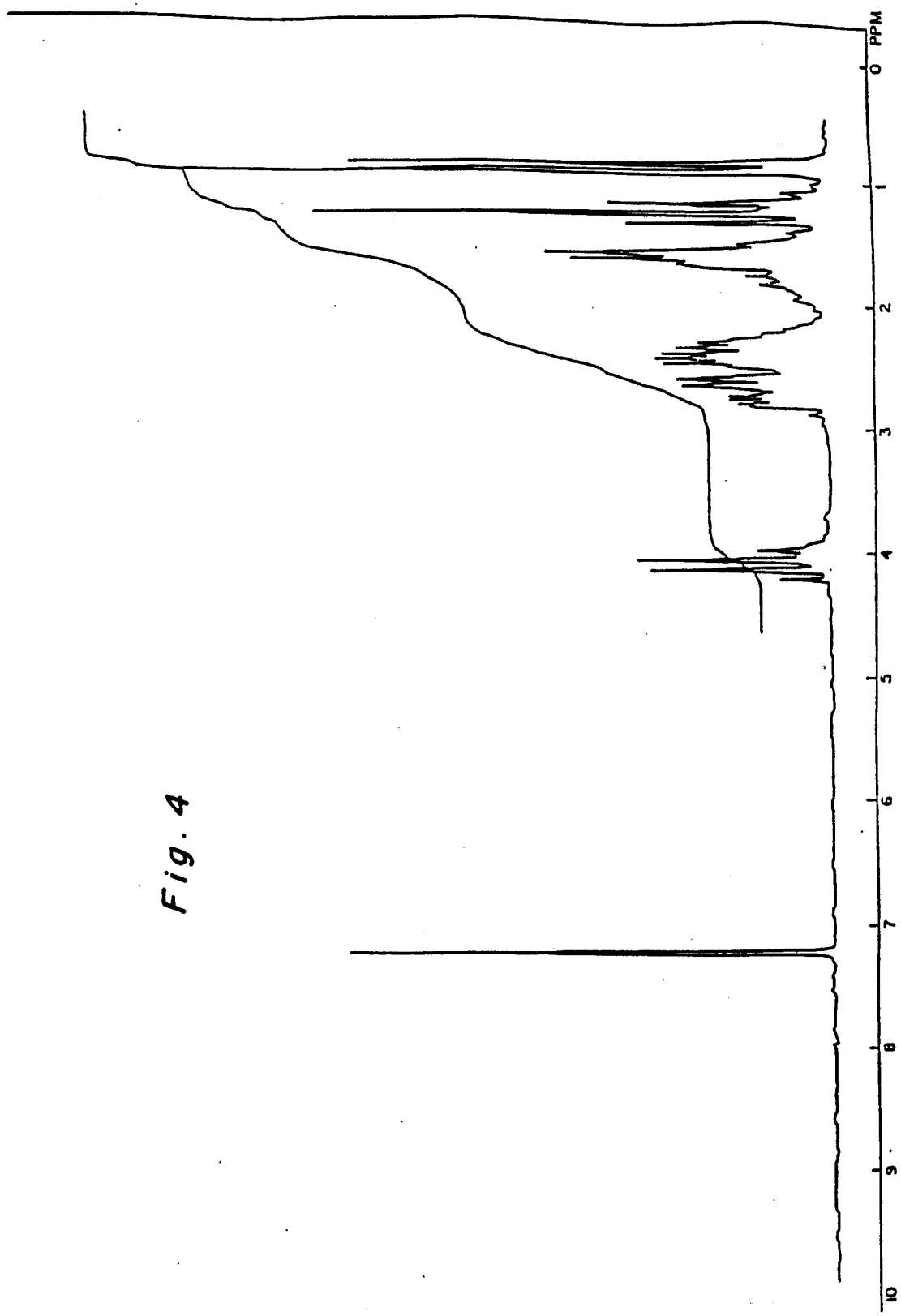
Figure 5:
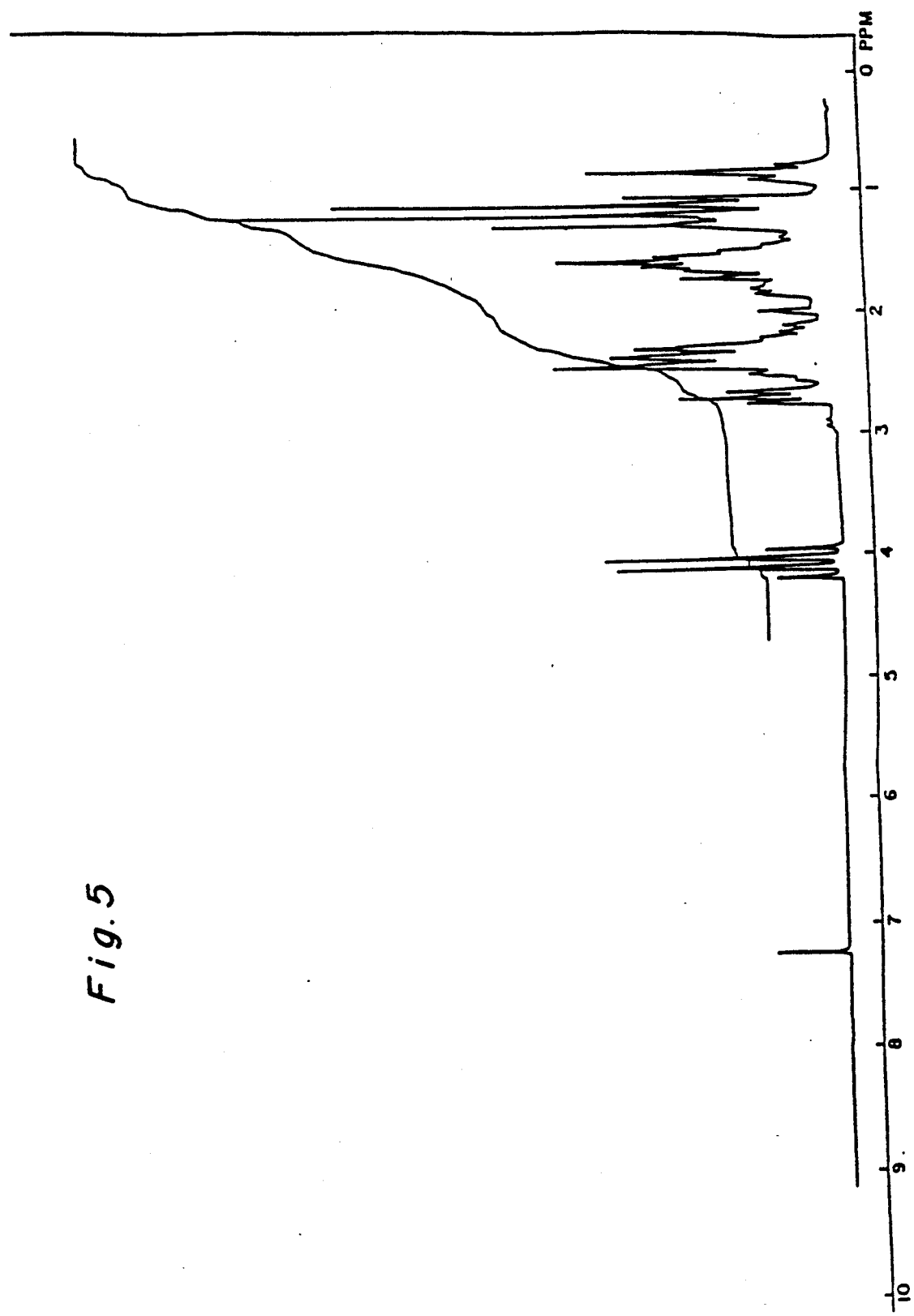
Figure 6:
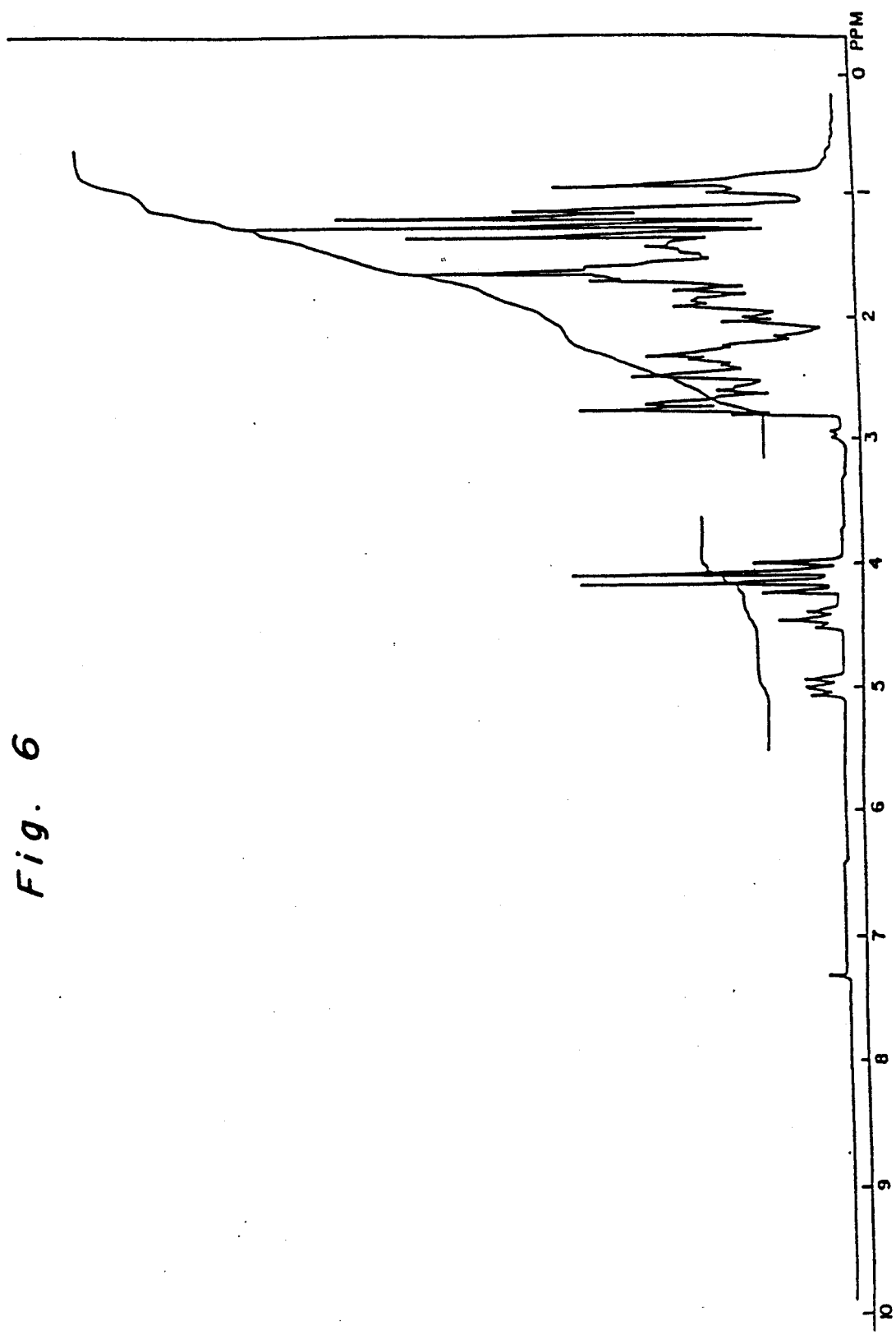
Figure 7:
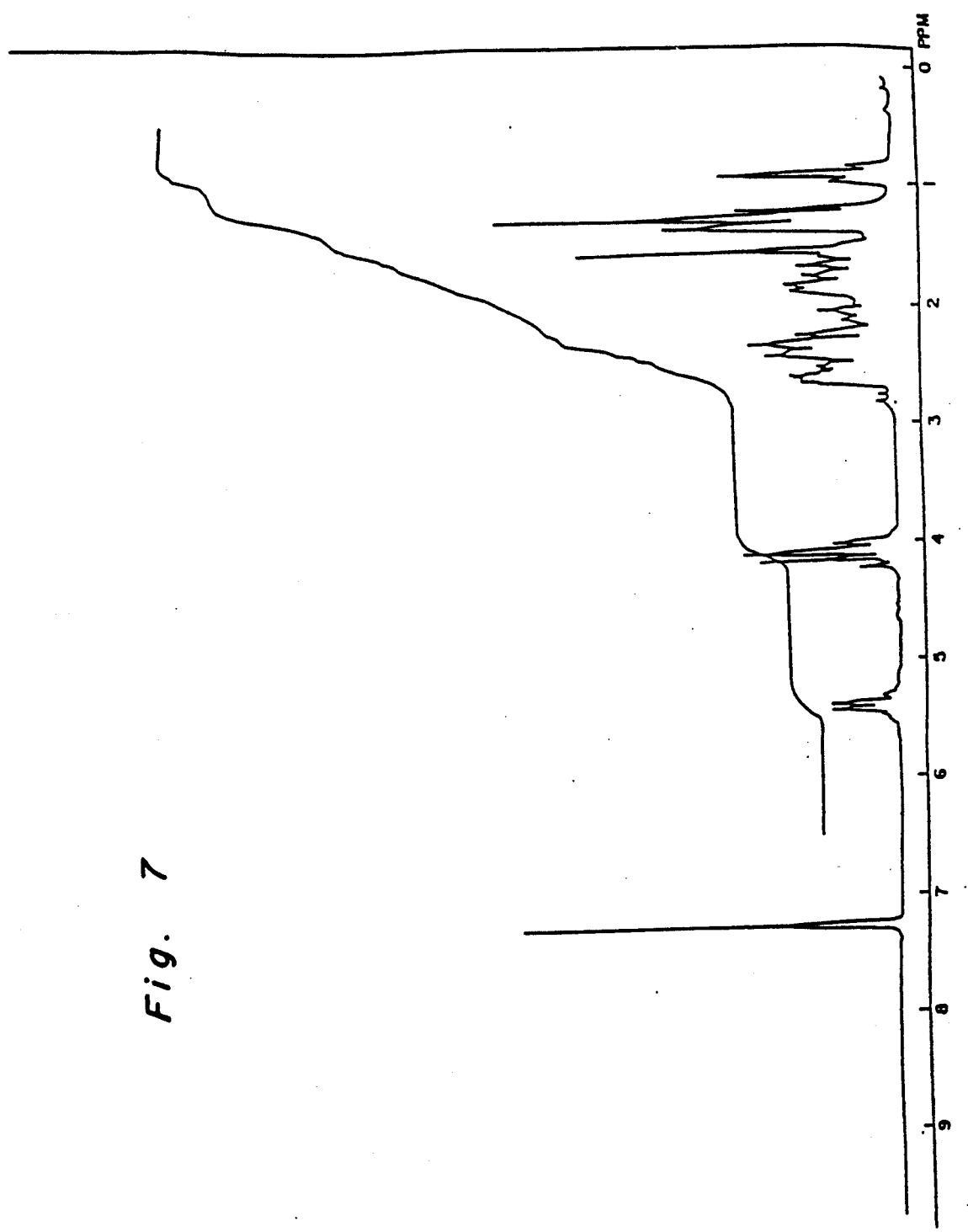
Figure 8:
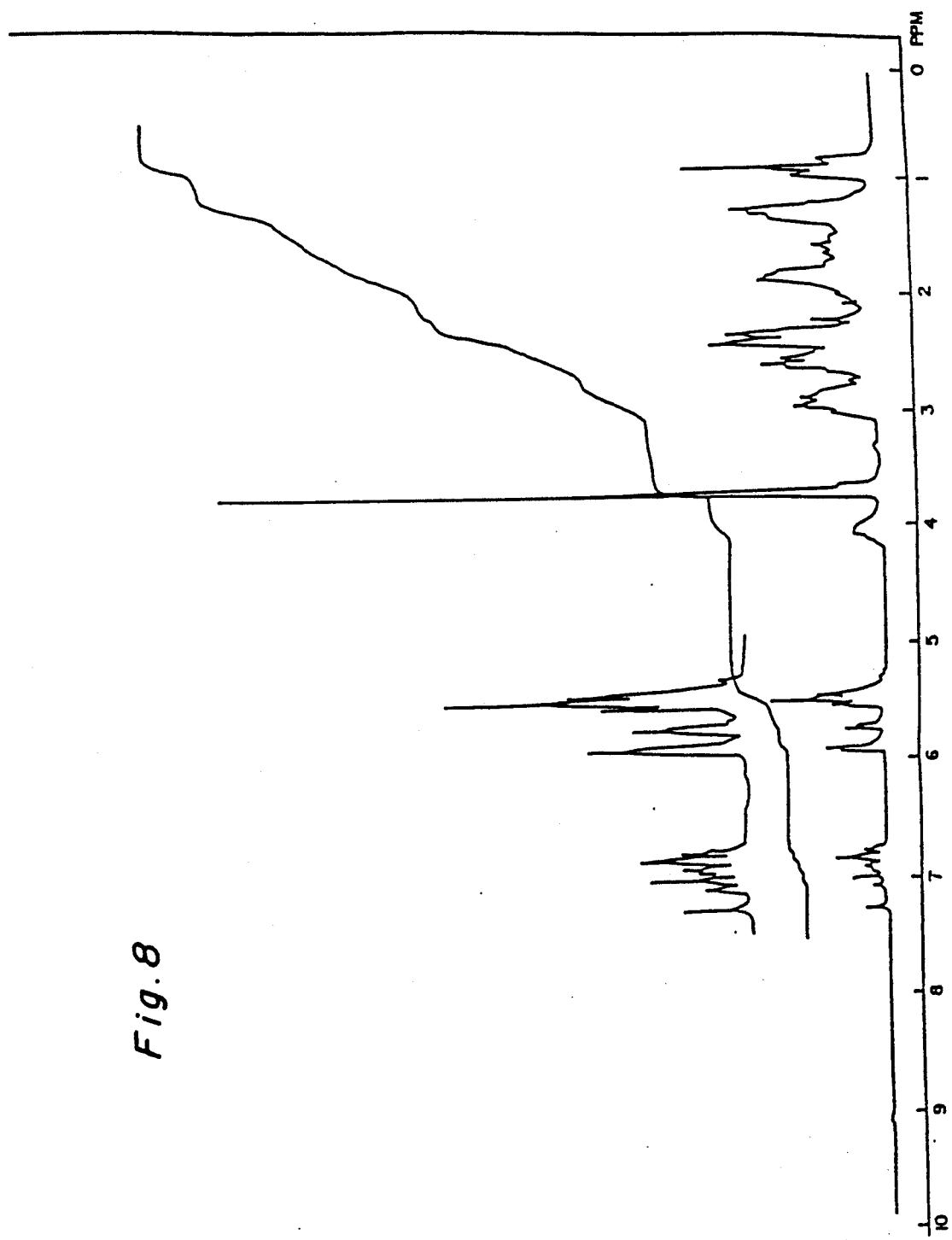

1: 13,14-dihydro-15-keto-PGE$_1$
2: 13,14-dihydro-15-keto-PGE$_1$ ethyl ester
3: 13,14-dihydro-15-keto-$\Delta^2$-PGE$_1$
4: 13,14-dihydro-15-keto-$\Delta^2$-PGE$_1$ methyl ester
5: 13,14-dihydro-15-keto-20-ethyl-PGE$_1$ methyl ester
6: 13,14-dihydro-6,15-diketo-PGE$_1$
7: 13,14-dihydro-6,15-diketo-PGE$_1$ methyl ester
8: 13,14-dihydro-6,15-diketo-PGE$_1$ ethyl ester
9: (±) 13,14-dihydro-6,15-diketo-PGE$_1$ ethyl ester
10: 13,14-dihydro-6,15-diketo-PGE$_1$ n-butyl ester
11: 13,14-dihydro-6,15-diketo-16R,S-methyl-PGE$_1$ methyl ester
12: 13.14-dihydro-6,15-diketo-16R,S-methyl-PGE$_1$ ethyl ester (FIG. 3)
13: 13,14-dihydro-6,15-diketo-16,16-dimethyl-PGE$_1$ ethyl ester
14: 13,14-dihydro-6,15-diketo-16R,S-fluoro-PGE$_1$ ethyl ester,
15: 13,14-dihydro-6,15-diketo-19-methyl-PGE$_1$ methyl ester
16: 13,14-dihydro-6,15-diketo-19-methyl-PGE$_1$ ethyl ester (FIG. 4)
17: 13,14-dihydro-6,15-diketo-11-dehydroxy-11R-hydroxymethyl-19-methyl-PGE$_1$ methyl ester
18: 13,14-dihydro-6,15-diketo-20-methyl-PGE$_1$ ethyl ester
19: 13,14-dihydro-6,15-diketo-11-dehydroxy-11R-methyl-PGE$_1$ methyl ester
20: 13,14-dihydro-6,15-diketo-11-dehydroxy-11R-methyl-PGE$_1$ ethyl ester (FIG. 5)
21: 13,14-dihydro-6,15-diketo-16R,S-fluoro-11R-dehydroxy-11R-methyl-PGE$_1$ ethyl ester (FIG. 6)
22: 13,14-dihydro-15-keto-PGE$_2$
23: 13,14-dihydro-15-keto-PGE$_2$ methyl ester
24: 13,14-dihydro-15-keto-PGE$_2$ ethyl ester (FIG. 7)
25: 13,14-dihydro-15-keto-PGE$_2$ n-propyl ester
26: 13,14-dihydro-15-keto-PGE$_2$ n-butyl ester
27: 13,14-dihydro-15-keto-PGE$_2$ benzyl ester
28: 13,14-dihydro-15-keto-PGE$_2$ hydroxyethyl ester
29: 13,14-dihydro-15-keto-$\Delta^2$-PGE$_2$-methyl ester (FIG. 8)

Figure 9:
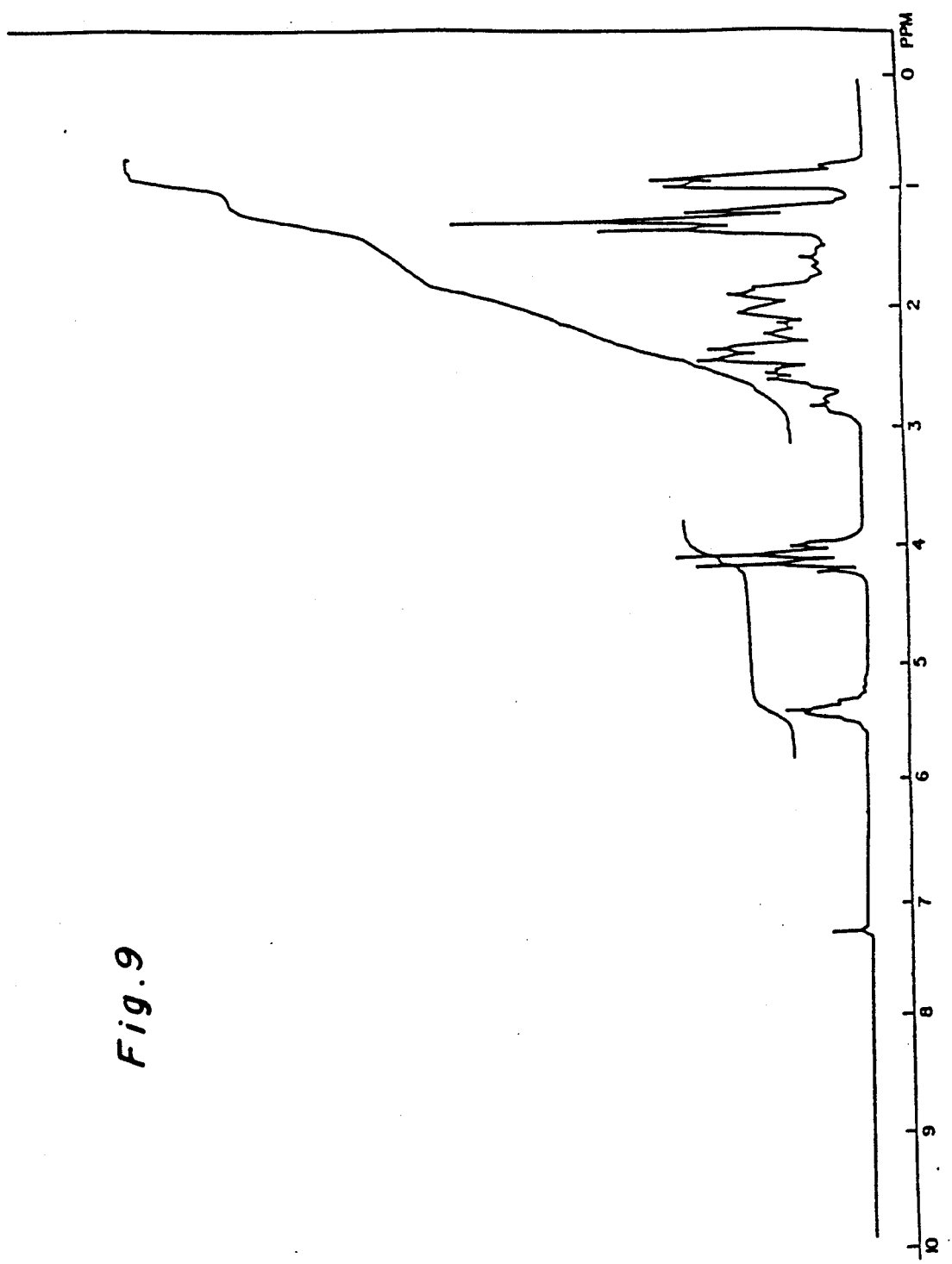
Figure 10:
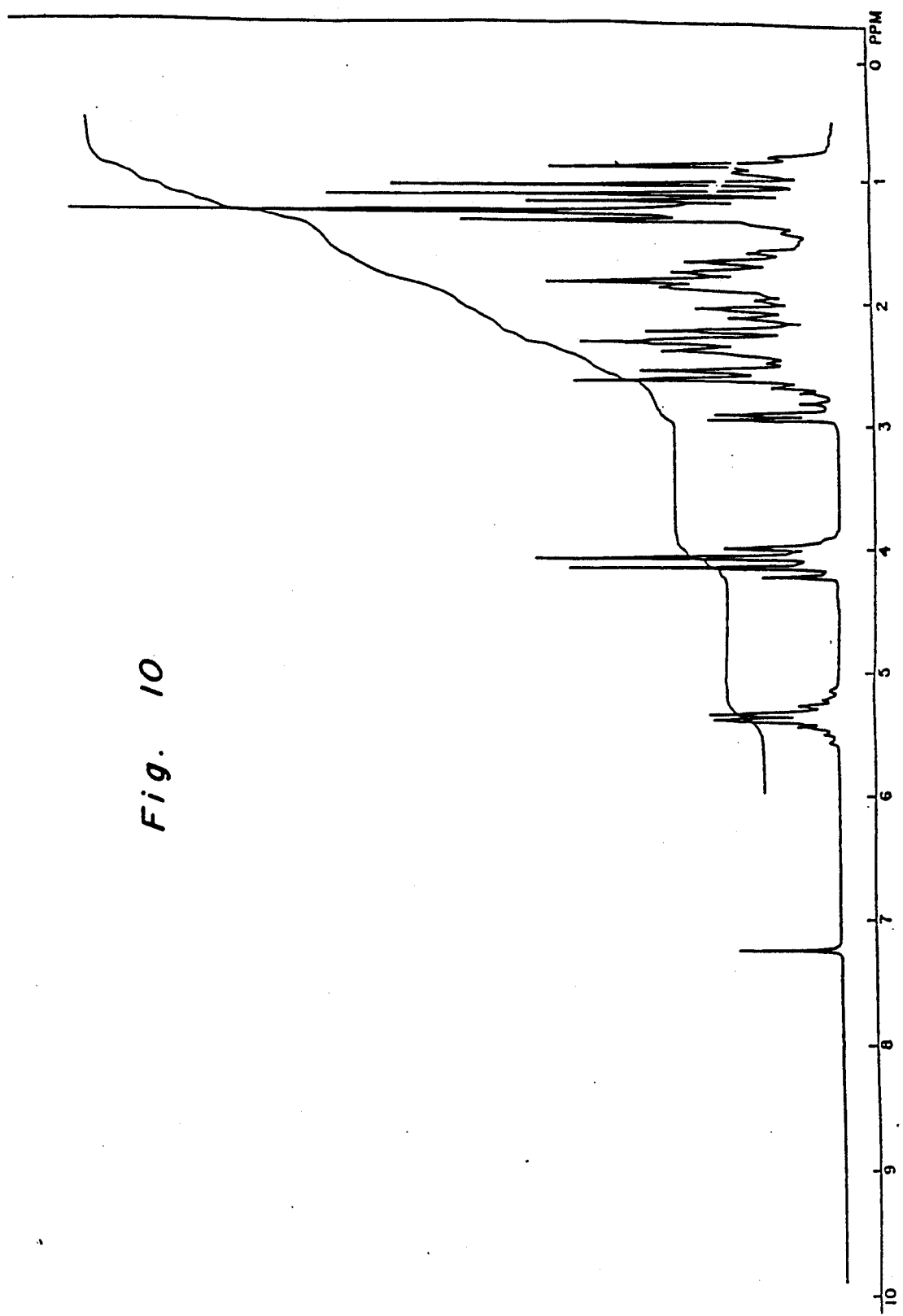
Figure 11:
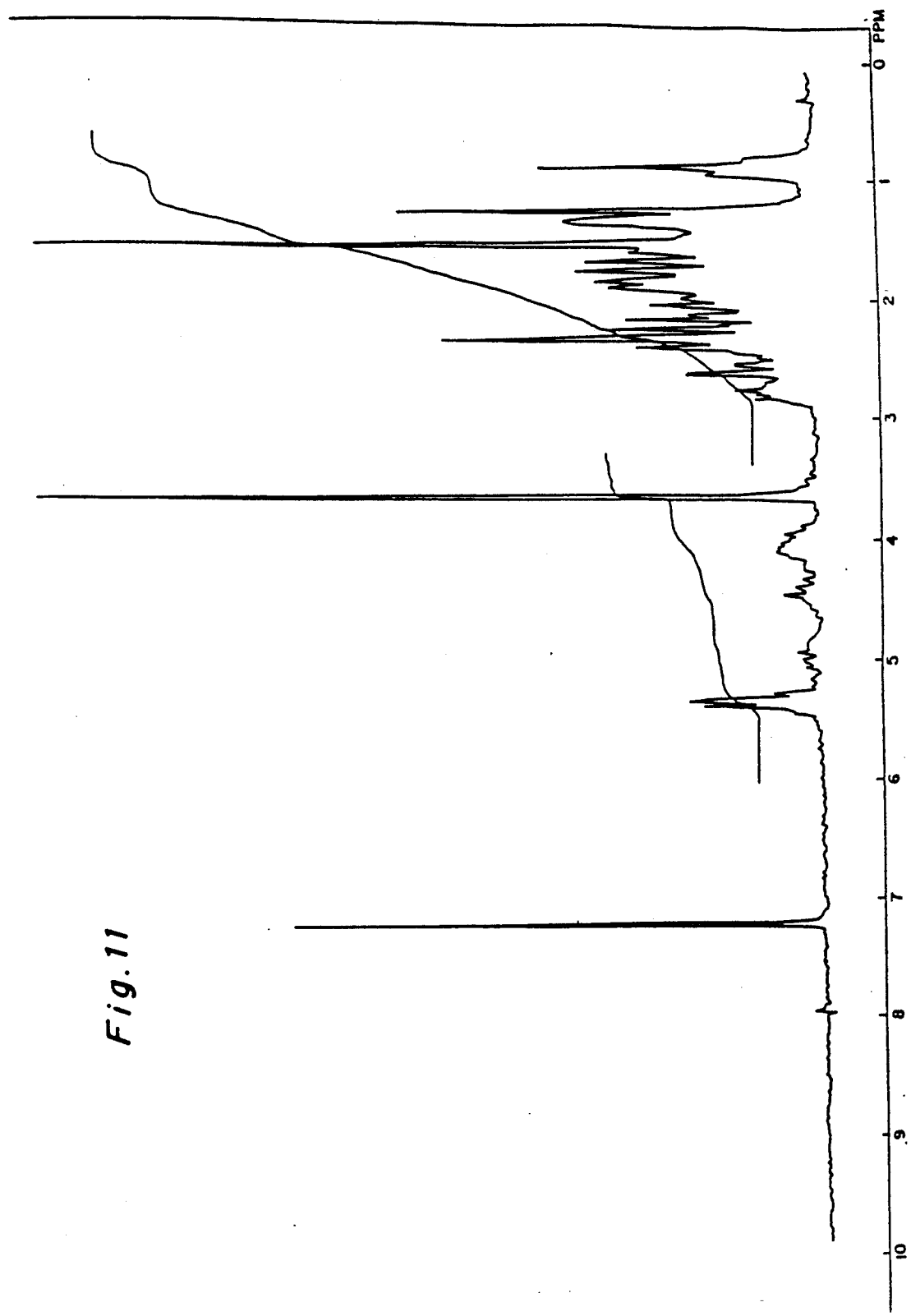
Figure 12:
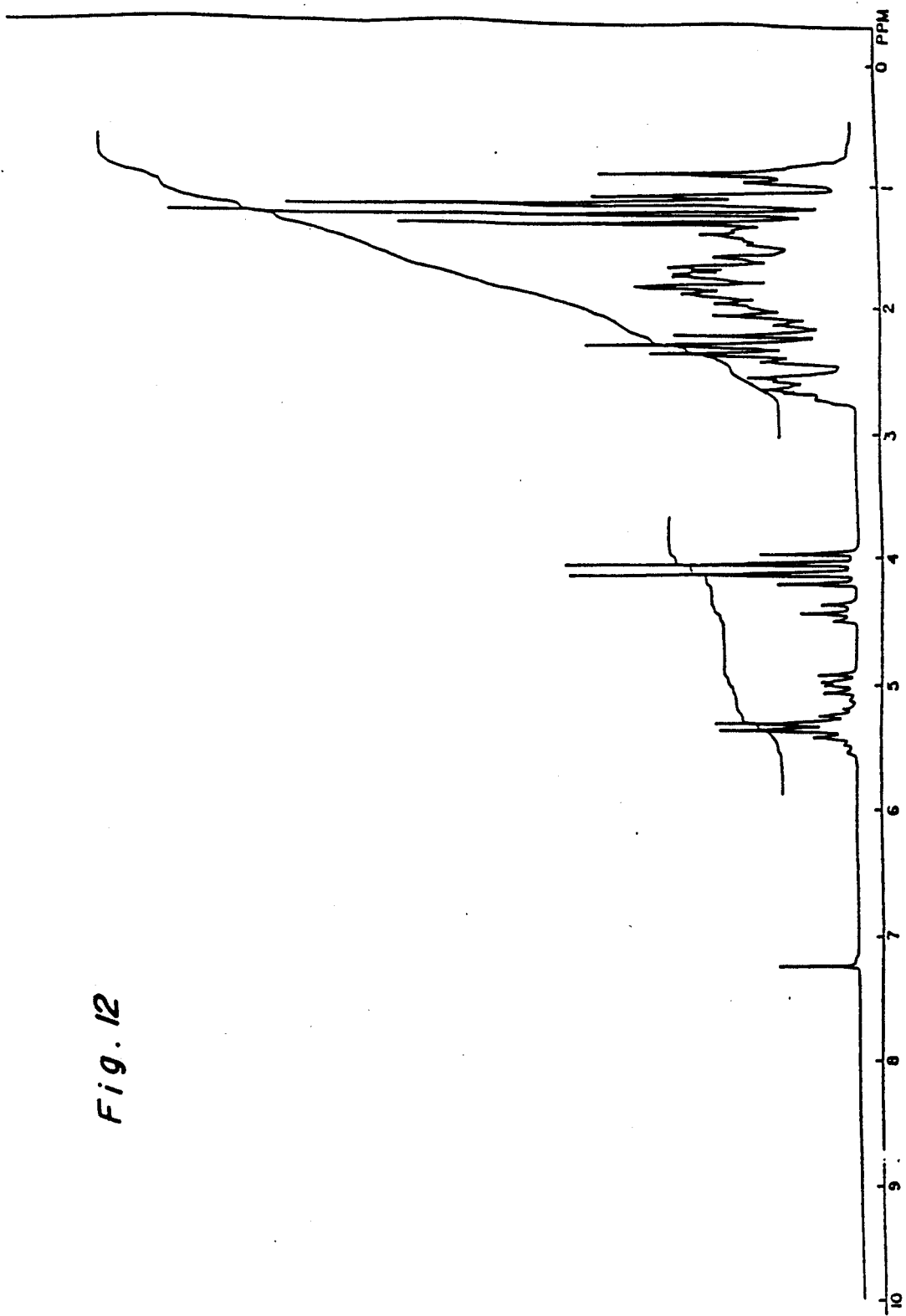
Figure 13:
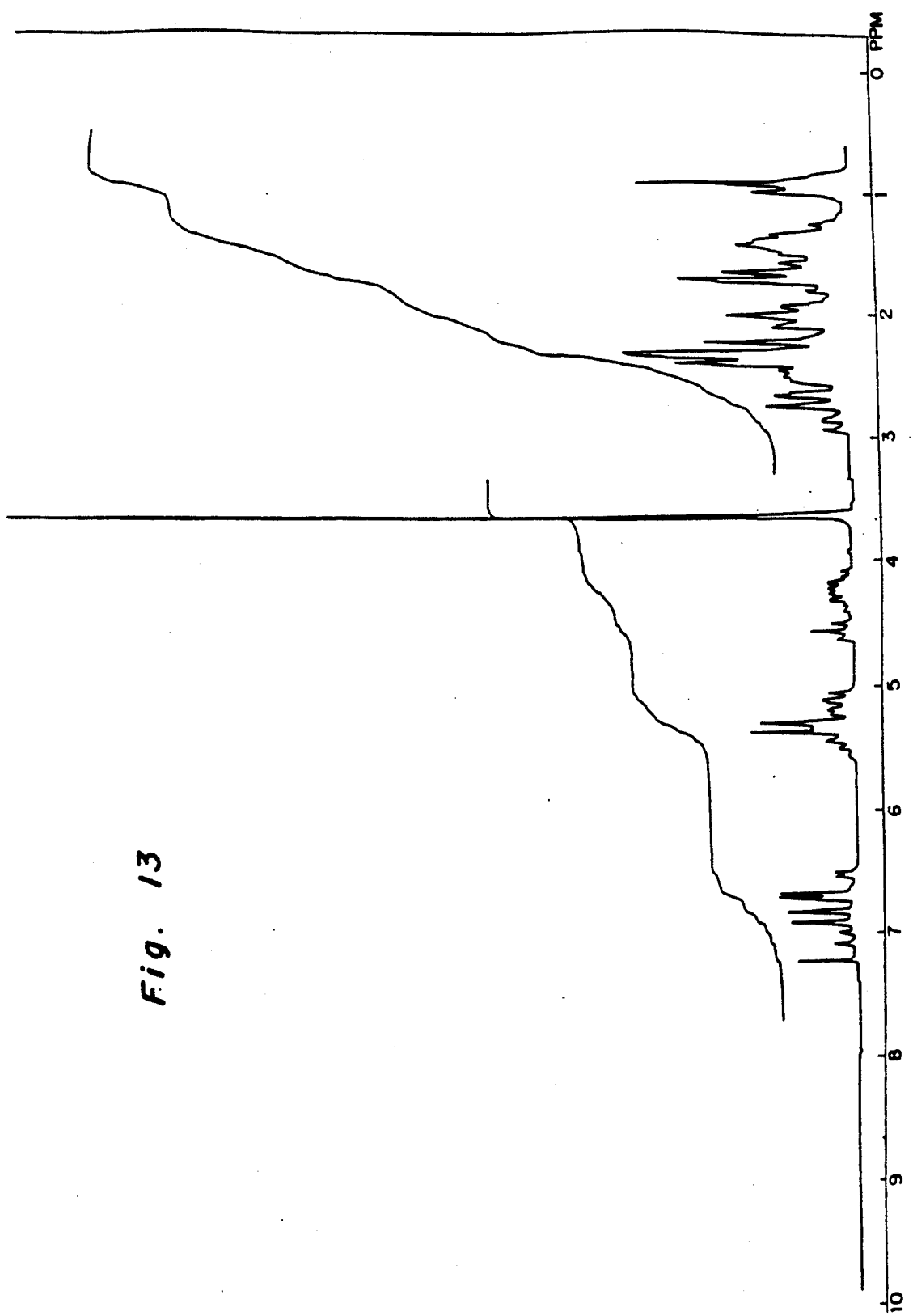

30: 13,14-dihydro-15-keto-3R,S-methyl-PGE$_2$ methyl ester
31: 13,14-dihydro-15-keto-3R,S-methyl-PGE$_2$ ethyl ester (FIG. 9)
32: 13,14-dihydro-15-keto-16R,S-methyl-PGE$_2$ methyl ester
33: 13,14-dihydro-15-keto-16R,S-methyl-PGE$_2$ ethyl ester (FIG. 10)
34: 13,14-dihydro-15-keto-3R,S,16R,S-dimethyl-PGE$_2$ methyl ester
35: 13,14-dihydro-15-keto-16,16-dimethyl-PGE$_2$ methyl ester
36: 13,14-dihydro-15-keto-16,16-dimethyl-PGE$_2$ ethyl ester
37: 13,14-dihydro-15-keto-16R,S-hydroxy-PGE ethyl ester
38: 13,14-dihydro-15-keto-16R,S-fluoro-PGE$_2$ (tautomeric isomer between carbonyl group at carbon atom of 15-position and hydroxyl group on carbon atom of 11-position is confirmed.)
39: 13,14-dihydro-15-keto-16R,S-fluoro-PGE$_2$ methyl ester
40: 13,14-dihydro-15-keto-16R,S-fluoro-PGE$_2$ ethyl ester
41: 13,14-dihydro-15-keto-16R,S-fluoro-20-methyl-PGE$_2$ methyl ester (FIG. 11)
42: 13,14-dihydro-15-keto-16R,S-fluoro-11-dehydroxy-11R-methyl-PGE$_2$ ethyl ester (FIG. 12)
43: 13,14-dihydro-15-keto-11-dehydroxy-11R-methyl-PGE$_2$ ethyl ester
44: 13,14-dihydro-15-keto-17S-methyl-PGE$_2$ methyl ester
45: 13,14-dihydro-15-keto-19-methyl-PGE$_2$ methyl ester
46: 13,14-dihydro-15-keto-19-methyl-PGE$_2$ ethyl ester
47: 13,14-dihydro-15-keto-20-methoxy-PGE$_2$ methyl ester
48: 13,14-dihydro-15-keto-20-methoxy-$\Delta^2$-PGE$_2$ methyl ester
49: 13,14-dihydro-15-keto-3R,S-methyl-20-methoxy-PGE$_2$ methyl ester
50: 13,14-dihydro-15-keto-16,16-dimethyl-20-methoxy-PGE$_2$ methyl ester
51: 13,14-dihydro-15-keto-20-isopropylidene-PGE$_2$
52: 13,14-dihydro-15-keto-20-isopropylidene-PGE$_2$ methyl ester
53: 13,14-dihydro-15-keto-20-ethyl-PGE$_2$ methyl ester
54: 13,14-dihydro-15-keto-20-ethyl-PGE$_2$ ethyl ester
55: 13,14-dihydro-15-keto-20-ethyl-11-dehydroxy-11R-methyl-PGE$_2$ methyl ester
56: 15-keto-16R,S-fluoro-PGE$_2$ methyl ester (FIG. 13)
57: PGE$_1$
58: PGE$_2$
59: PGE$_2$ methyl ester
60: 15-keto-17S-methyl-PGE$_2$ ethyl ester
61: 15-keto-PGE$_2$ isopropyl ester
62: 6,15-diketo-19-methyl-PGE$_1$ ethyl ester As shown in Table 2, 15-keto-PGEs obviously show fervescence activity even by peripheral administration such as intravenous injection.

EXAMPLE 3

Experiment was carried out in the same manner as in Example 2 except for that test drugs were administered intravenously with a dose of 5 mg/kg. The results are shown in Table 3.

TABLE 3

| Test Drug | Rising of body temperature (°C.) |
|---|---|
| 25 | +1.3 |
| 26 | +0.9 |
| 62 | +0.63 |

EXAMPLE 4 fervescence (recovery of body temperature) activity at hemorrhage load

Wister male rats (weight: 200 g) were subcutaneously injected on the back with 1.5 g/kg of urethane, subjected to anesthesia. Hemorrhage was then induced by withdrawal of blood by puncture of the heart for the total volume of 3 ml equivalent to 1.5% of the body weight. After kept in a room for 60 minutes, the rats were administered intravenously with test solutions prepared by dissolving test drugs into Ringer's solution so as to administer the rat at a dose of 0.5 or 1 mg/kg, and change of the body temperature was observed. Ringer's solution was administered as control.

Figure 2:
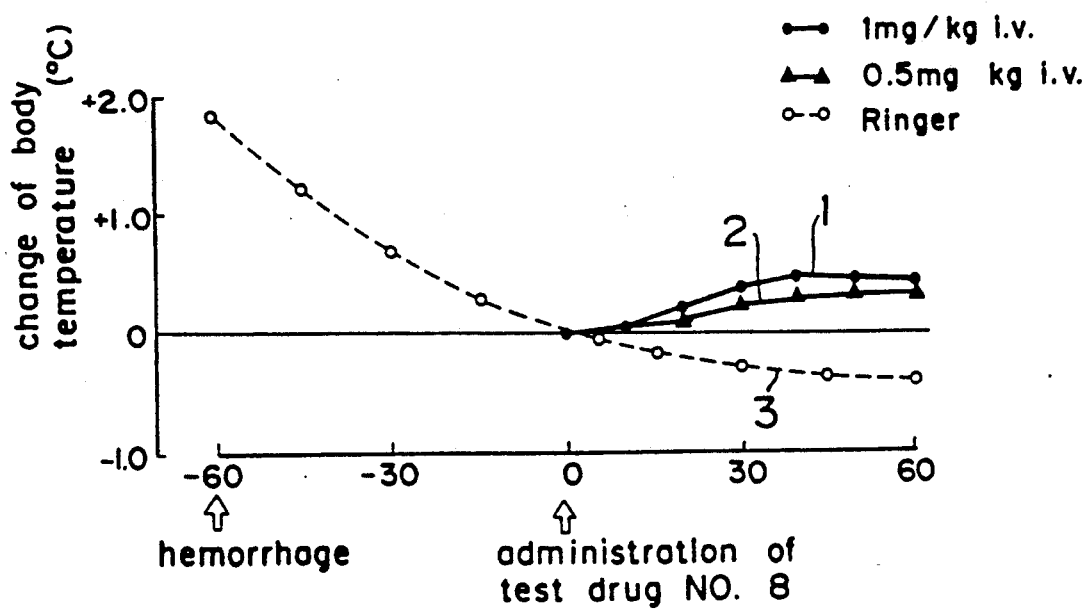
FIG. 2 shows change of body temperature before and after administration of a test drug 8, (13,14-dihydro-6,15-diketo-$PGE_1$ ethyl ester) to a rat loaded with bloodletting.

The results are shown in Table 4 and FIGS. 1 and 2.

TABLE 4

(Fervescence Activity on the Rat Loaded with Hemorrhage)

| | Rising of Body Temperature (°C) | |
|---|---|---|
| Test Drug | 0.5 mg/kg | 1 mg/kg |
| 8 | +0.7 | +0.8 |
| 16 | +0.4 | +0.6 |
| 18 | +0.4 | +0.8 |
| 20 | +0.5 | +0.8 |
| 24 | +0.8 | +1.1 |
| Control | 0 | |

FIG. 1 shows change of body temperature before and after administration of a test drug 24, (13,14-dihydro-15-keto-PGE$_2$ ethyl ester) to a rat loaded with hemorrhage.

FIG. 2 shows change of body temperature before and after administration of a test drug 8, (13,14-dihydro-6,15-diketo-PGE$_1$ ethyl ester) to a rat loaded with hemorrhage.

In the figures, (1), (2) and (3) correspond to the results of administration of doses 1 mg/kg, 0.5 mg/kg and Ringer's solution alone, respectively.

Obviously shown in Table 4 and FIGS. 1 and 2, the group of rats administered with the 15-keto-PGEs of this invention are observed doseresponse fervescence although body temperature continued to fall after the administration in the group administered with Ringer's solutions.

The compound of this invention is useful as drug for recovering body temperature from hypothermia caused by serious bleeding and surgery from the above results, since they proved the fervescence activity of the compound to the animals under the condition of low body temperature (33° C.) being unable to maintain the normal body temperature by bleeding, namely, out of homeostasis.

EXAMPLE 5

Sedation Activity

A 19-methyl type compound having strong fervescence activity was compared with PGE$_2$ emthyl ester in sedation activity. A hybrid adult dog was held on a holder for dog and intravenously administered with a test drug dissolved in Ringer's solutions at the forefoot.

Sedation activity was judged as follows:

Sedation Degree
1: Disappearance of body movement
2: Closing of the eyes
3: Leaning on the holding belt

TABLE 5

| Test Drug | Dose mg/kg | Rising of Body Temperature (°C.) | Sedation Degree | | |
|---|---|---|---|---|---|
| | | | 1 | 2 | 3 |
| 45 | 0.5 | 0.5 | — | — | — |
| 15 | 0.5 | 1.2 | — | — | — |
| 16 | 0.5 | 1.1 | — | — | — |
| 59 | 0.01 | 0.4 | + | + | + |

Obviously shown in the results in Table 5, the test drugs of this invention show no sedation activity although $PGE_2$ methyl ester shows clear sedation activity.

EXAMPLE 6 acute toxicity

Acute toxicity ($LD_{50}$) of the test drugs was estimated on Slc-ddY female mice (5-weeks old) by an intravenous injection. Results are shown in Table 6.

TABLE 6

| test drug | $LD_{50}$ mg/kg |
|---|---|
| 2 | >1000 |
| 16 | >300 |
| 23 | >1000 |

TABLE 6-continued

| test drug | $LD_{50}$ mg/kg |
|---|---|
| 24 | 1000 |

The 15-keto-PGEs of this invention have fervescense activity and the compound in the ester shows the activity by peripheral administration such as intravenous injection or oral administration in the same manner as by intracerebroventricular injection. It brings on improvement of body mechanism such as fervescence activity on an animal in the shock condition and being unable to maintain the normal body mechanism such as body temperature by, for example, bleeding, namely, out of homeostasis.

Accordingly, the 15-keto-PGEs of this invention is useful as a drug for recovering from hypothermia occurred after hypothermic operation such as surgical operation, hypothermia accompanied with a decline of basal metabolism ratio by such as thyroid hormone hyposecretion, hypothermia by disorder of the brain, hypothermia caused by serious bleeding and disorder or consciousness, hypothermia caused by lowering of the surrounding temperature, hypothermia caused by heat-loss from the surface of the body by such as sweating and vasodilation, hypothermia and asphyxiation, and also useful as a drug for rising the body temperature falling under the shock condition to recover various body mechanisms for removal from the shock state and improve the homeostasis and maintaining ability. Additionally, it is useful as a drug for preventing the above hypothermias.

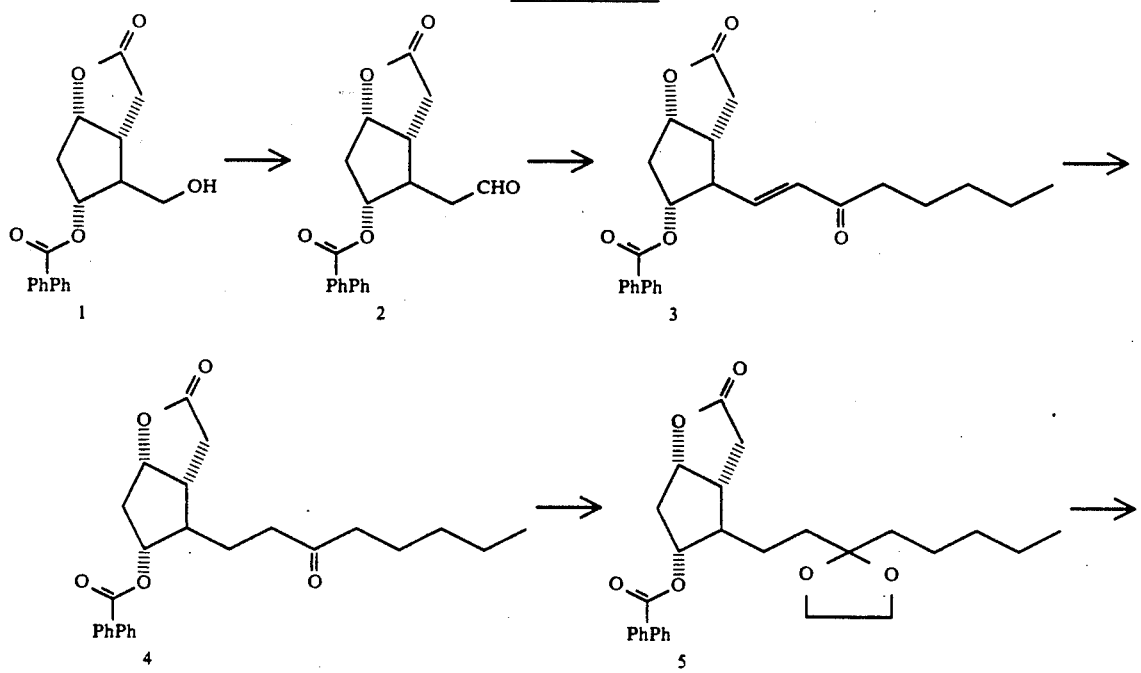

Synthetic Chart I

-continued
Synthetic Chart I
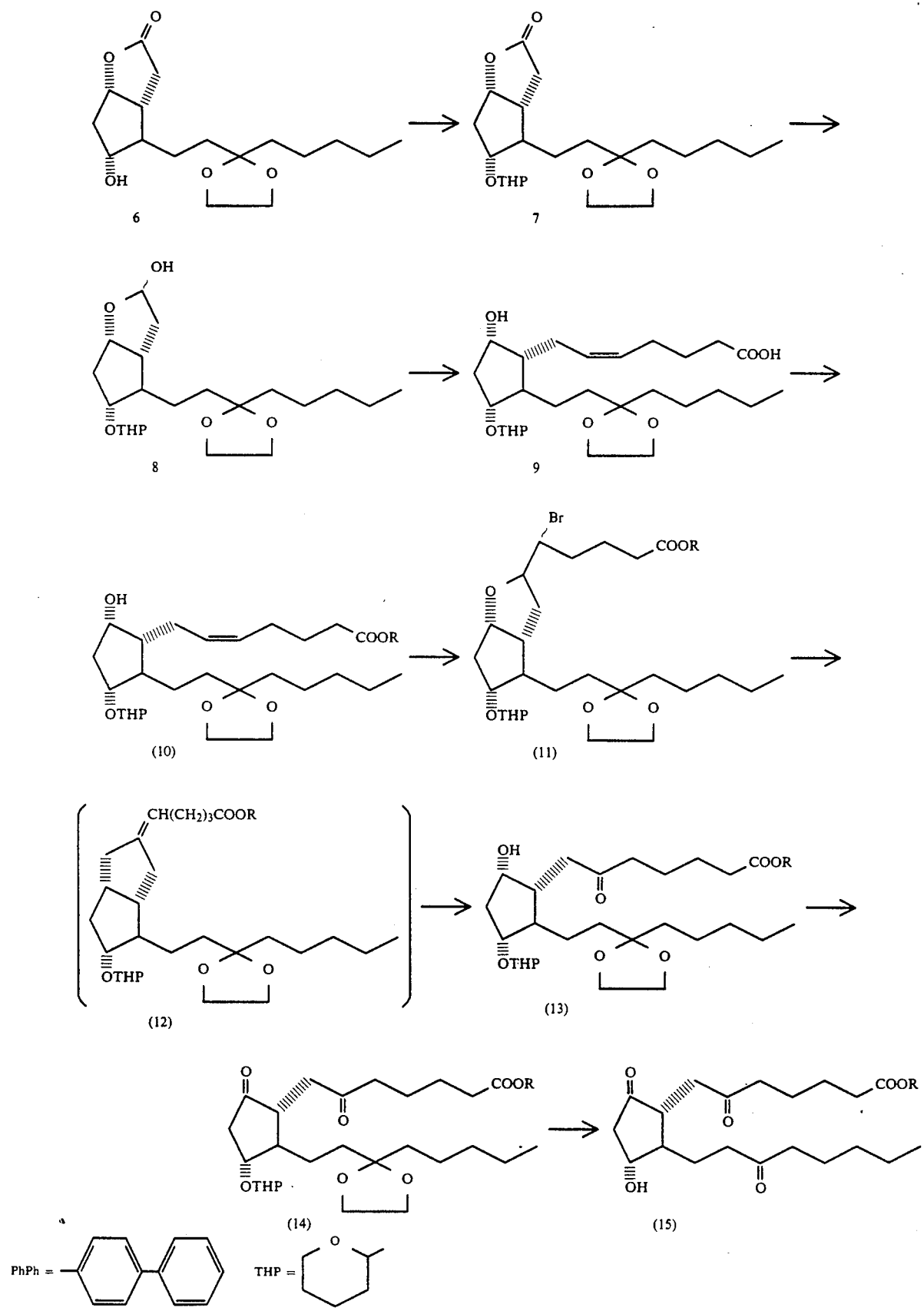
PhPh = [biphenyl structure]   THP = [tetrahydropyranyl structure]

Synthetic Chart II
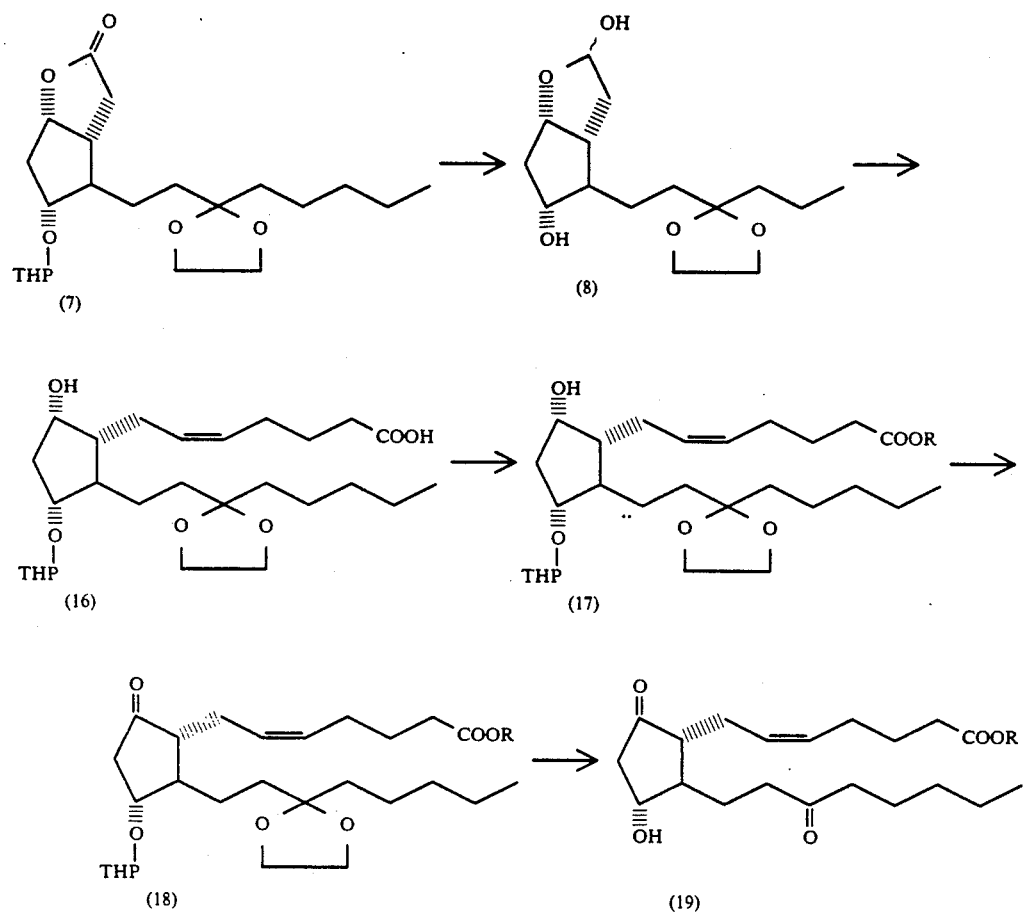
Synthetic Chart III
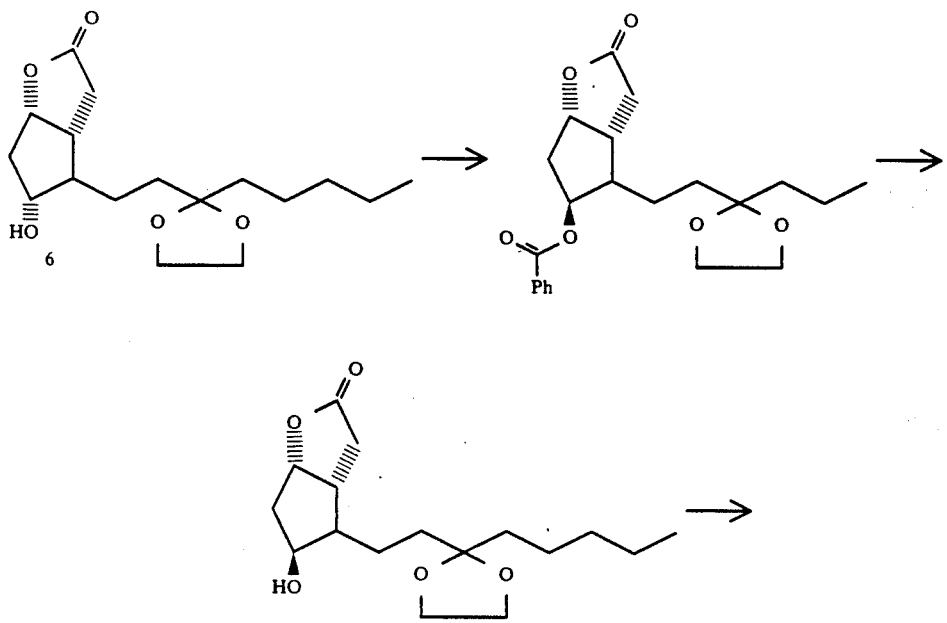

-continued
Synthetic Chart III

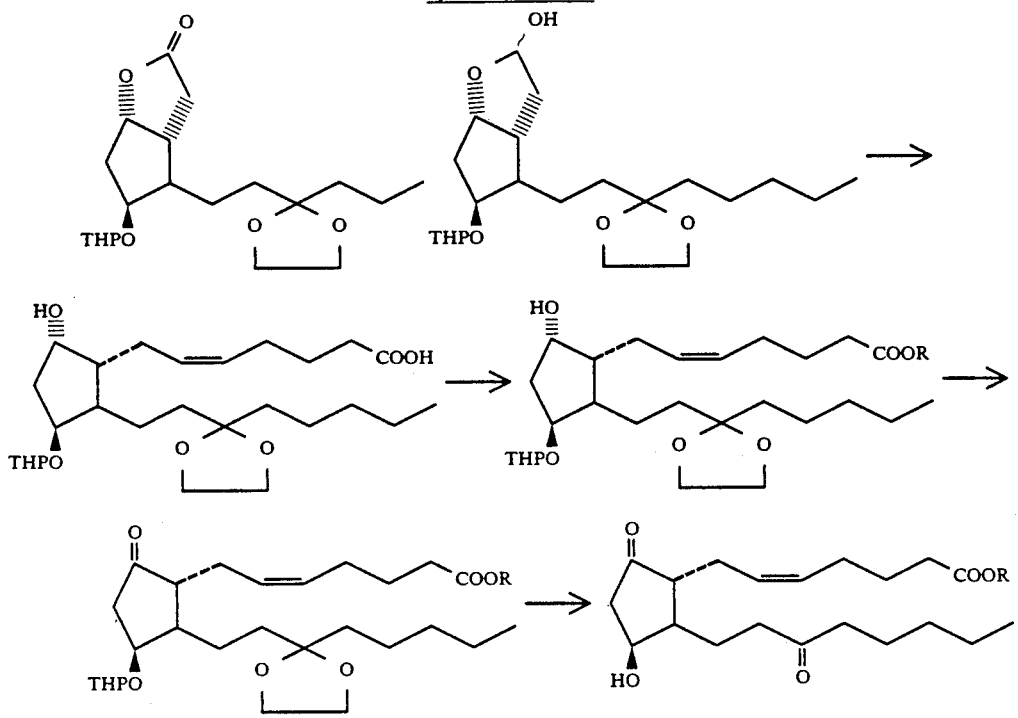

What is claimed is:

1. A method for treating hypothermia which comprises administering to a patient in need of such treatment a hypothermia treating effective amount of a 15-keto-PGE.

2. The method of claim 1, in which the 15-keto-PGE is represented by the following formula:

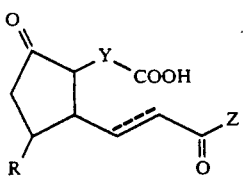

wherein R is a hydroxyl group, a hydroxyalkyl group, or an alkyl group; Y is a saturated or an unsaturated hydrocarbon moiety having 2-6 carbon atoms wherein a portion of carbon atoms constituting the hydrocarbon moiety may be carbonyl or hydrocarbon moiety may be substituted with other atoms or groups; Z is a saturated or an unsaturated hydrocarbon moiety having 1-10 carbon atoms which may constitute a ring or the hydrocarbon moiety may be substituted with other atoms or groups;

physiologically acceptable salts or esters thereof.

3. A method in accordance with claim 2, wherein the 15-keto-PGE is a 13,14-dihydro-15-keto-PGE.

4. The method of claim 1, in which the hydrocarbon moiety represented by Z is substituted with a group or atom selected from a hydroxyl group, an alkyl group, a phenyl group, an alkoxy group, a phenoxy group or a halogen atom.

5. A method in accordance with claim 4, wherein the 15-keto-PGE is a 13,14-dihydro-15-keto-PGE.

6. The method of claim 1, in which the 13,14-dihydro-15-keto-PGE is an ester thereof.

7. A method in accordance with claim 6, wherein the 15-keto-PGE is a 13,14-dihydro-15-keto-PGE.

8. The method of claim 1, in which Z represents a formula: $-CH_2CH_2CH_2CH(R_1)(R_2)$: wherein $R_1$ is a hydrogen atom or a methyl group, and $R_2$ is a methyl group, an ethyl group or a propyl group.

9. A method in accordance with claim 8, wherein the 15-keto-PGE is a 13,14-dihydro-15-keto-PGE.

10. The method of claim 1, wherein Z is a fluoroalkyl group.

11. A method in accordance with claim 10, wherein the 15-keto-PGE is a 13,14-dihydro-15-keto-PGE.

12. A method in accordance with claim 1, wherein the 15-keto-PGE is a 13.14-dihydro-15-keto-PGE.

13. The method of claim 12, wherein the 13,14-dihydro-15-keto-PGE is a 13,14-dihydro-15-19-methyl-PGE.

14. The method of claim 12, wherein the 13,14-dihydro-15-keto-PGE is a 13,14-dihydro-15-keto-16R,S-fluoro-PGE.

15. The method of claim 12, wherein the 13,14-dihydro-15-keto-PGE is a 13,14-dihydro-15-keto-16R,S-fluoro-11-dehydroxy-11R-methyl-PGE.

16. The method of claim 12, wherein the 13,14-dihydro-15-keto-PGE is a 13,14-dihydro-15-keto-3R,S-methyl-PGE.

17. The method of claim 12, wherein the 13,14-dihydro-15-keto-PGE is a 13,14-dihydro-15-keto-16R,S-methyl-PGE.

18. The method of claim 12, wherein the 13,14-dihydro-15-keto-PGE is a 13,14-dihydro-15-keto-6,16-diketo $PGE_1$.

19. A method for treating hypothermia as in claim 12, wherein the 13,14-dihydro-15-keto-PGE is 13,14-dihydro-6,15-diketo-19-methyl-$PGE_1$ ethyl ester.

20. The hypothermia treating method of claim 1, wherein the PGE is administered in an amount effective for increasing body temperature of said patient.

21. The hypothermia treating method of claim 1, wherein the PGE is administered in an amount effective for said patient to recover body temperature.

22. A method for preventing hypothermia which comprises administering to a patient in need of such prevention a hypothermia preventing effective amount of a 15-keto-PGE.

23. The hypothermia preventing method of claim 22, wherein the PGE is administered in an amount effective for increasing body temperature of said patient.

24. The hypothermia preventing method of claim 22, wherein the PGE is administered in an amount effective for said patient to recover body temperature.

25. The method of claim 22, in which the 15-keto-PGE is represented by the following formula:

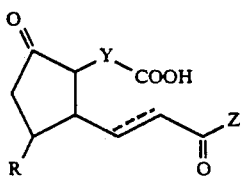

wherein R is a hydroxyl group, a hydroxyalkyl group, or an alkyl group; Y is a saturated or an unsaturated hydrocarbon moiety having 2-6 carbon atoms wherein a portion of carbon atoms constituting the hydrocarbon moiety may be carbonyl or hydrocarbon moiety may be substituted with other atoms or groups; Z is a saturated or an unsaturated hydrocarbon moiety having 1-10 carbon atoms which may constitute a ring or the hydrocarbon moiety may be substituted with other atoms or groups;

physiologically acceptable salts or esters thereof.

26. A method in accordance with claim 25, wherein the 15-keto-PGE is a 13,14-dihydro-15-keto-PGE.

27. The method of claim 22, in which the hydrocarbon moiety represented by Z is substituted with a group or atom selected from a hydroxyl group, an alkyl group, a phenyl group, an alkoxy group, a phenoxy group or a halogen atom.

28. A method in accordance with claim 27, wherein the 15-keto-PGE is a 13,14-dihydro-15-keto-PGE.

29. The method of claim 22, in which the 15-keto-PGE is an ester thereof.

30. A method in accordance with claim 29, wherein the 15-keto-PGE is a 13,14-dihydro-15-keto-PGE.

31. The method of claim 22, in which Z represents a formula: $-CH_2CH_2CH_2CH(R_1)(R_2)$: wherein $R_1$ is a hydrogen atom or a methyl group, and $R_2$ is a methyl group, an ethyl group or a propyl group.

32. A method in accordance with claim 31, wherein the 15-keto-PGE is a 13,14-dihydro-15-keto-PGE.

33. The method of claim 22, wherein Z is a fluoroalkyl group.

34. A method in accordance with claim 33, wherein the 15-keto-PGE is a 13,14-dihydro-15-keto-PGE.

35. A method in accordance with claim 22, wherein the 15-keto-PGE is a 13,14-dihydro-15-keto-PGE.

36. The method of claim 35, wherein the 13,14-dihydro-15-keto-PGE is a 13,14-dihydro-15-keto-19-methyl-PGE.

37. The method of claim 35, wherein the 13,14-dihydro-15-keto-PGE is a 13,14-dihydro-15-keto-16R,S-fluoro-PGE.

38. The method of claim 35, wherein the 13,14-dihydro-15-keto-PGE is a 13,14-dihydro-15-keto-16R,S-fluoro-11-dehydroxy-11R-methyl-PGE.

39. The method of claim 35, wherein the 13,14-dihydro-15-keto PGE is a 13,14-dihydro-15-keto-3R,S-methyl-PGE.

40. The method of claim 35, wherein the 13,14-dihydro-15-keto PGE is a 13,14-dihydro-15-keto-16R,S-methyl-PGE.

41. The method of claim 35, wherein the 13,14-dihydro-15-keto PGE is a 13,14-dihydro-15-keto-6,16-diketo $PGE_1$.

42. A method for preventing hypothermia as in claim 35, wherein the 13,14-dihydro-15-keto-PGE is 13,14-dihydro-6,15-diketo-19-methyl-$PGE_1$ ethyl ester.

* * * * *